(12) United States Patent
Tkachuk

(10) Patent No.: US 8,665,424 B2
(45) Date of Patent: Mar. 4, 2014

(54) OPTICAL ABSORPTION GAS ANALYSER

(75) Inventor: Michael Tkachuk, Sayville, NY (US)

(73) Assignee: BAH Holdings LLC, Glen Cove, NY (US)

( * ) Notice: Subject to any disclaimer, the term of this patent is extended or adjusted under 35 U.S.C. 154(b) by 446 days.

(21) Appl. No.: 12/944,683

(22) Filed: Nov. 11, 2010

(65) Prior Publication Data

US 2011/0116079 A1    May 19, 2011

(30) Foreign Application Priority Data

Nov. 12, 2009   (GB) .................................. 0919794.8

(51) Int. Cl.

| | | |
|---|---|---|
| *G01J 3/00* | (2006.01) | |
| *G01J 5/00* | (2006.01) | |
| *G01N 21/00* | (2006.01) | |
| *G01J 5/48* | (2006.01) | |
| *G01K 1/08* | (2006.01) | |
| *G01K 1/14* | (2006.01) | |
| *G01K 13/00* | (2006.01) | |

(52) U.S. Cl.
USPC ............... 356/51; 356/73; 356/432; 356/433; 356/44; 374/141; 374/123

(58) Field of Classification Search
USPC .............. 356/73, 437, 432, 433, 44; 374/123, 374/141
See application file for complete search history.

(56) References Cited

U.S. PATENT DOCUMENTS

| | | | | |
|---|---|---|---|---|
| 3,329,005 A | * | 7/1967 | Levy et al. .................... | 73/23.23 |
| 5,886,348 A | * | 3/1999 | Lessure et al. ........... | 250/339.13 |
| 2002/0063216 A1 | * | 5/2002 | Clausen et al. ............... | 250/343 |
| 2009/0235720 A1 | * | 9/2009 | Smith .......................... | 73/31.05 |
| 2009/0268204 A1 | * | 10/2009 | Tkachuk ....................... | 356/437 |

FOREIGN PATENT DOCUMENTS

| | | | | |
|---|---|---|---|---|
| EP | 1922532 | | 2/2007 | |
| EP | 1987346 | | 8/2007 | |
| JP | 62261032 | * | 5/1986 | ............ G01N 21/27 |
| JP | 01049937 | | 2/1989 | |
| WO | 2009019467 | | 2/2009 | |

OTHER PUBLICATIONS

Search Report for corresponding Great Britain Application No. GB0919794.8 dated Nov. 25, 2009.

* cited by examiner

*Primary Examiner* — Tarifur Chowdhury
*Assistant Examiner* — Sunghee Y Gray
(74) *Attorney, Agent, or Firm* — James P. Muraff; Neal, Gerber & Eisenberg LLP

(57) ABSTRACT

An optical absorption gas analyzer is provided for determining the concentration of a target gas in a sample, comprising: a chamber for containing the sample in use; an optopair, comprising a light emitting diode (LED) arranged to emit radiation into the chamber and a photovoltaic radiation detector arranged to detect radiation transmitted through the chamber from the LED and to output a corresponding detection signal $S_S$; a temperature sensor arranged in thermal contact with the LED and the photovoltaic radiation detector, and to output a temperature signal T representing the temperature of the optopair; a memory having stored therein data representative of the baseline detection signal $S_T$ output by the optopair in the absence of the target gas as a function of the temperature of the optopair across a range of temperatures; and a processor adapted to generate a differential detection signal $S_A$ indicative of the concentration of target gas in the sample by retrieving from the memory the baseline detection signal $S_T$ corresponding to the temperature signal T and calculating the difference between the detection signal $S_S$ and the baseline detection signal $S_T$.

27 Claims, 3 Drawing Sheets

OPTICAL ABSORPTION GAS ANALYSER

CROSS-REFERENCE TO RELATED PATENT APPLICATIONS

This application claims the benefit of Great Britain Patent Application No. 0919794.8 filed on Nov. 12, 2009, the disclosure of which is incorporated herein in its entirety by reference.

This invention relates to an improved, low cost and low power instrument for the measurement of concentration of a target gas by means of optical absorption. In particular, the invention relates to apparatus and methods for non-dispersive infrared (NDIR) measurement based on the absorption of radiation by the gas of interest.

Optical absorption techniques such as non-dispersive infrared (NDIR) measurement have been recognized for many years as sensitive, stable and reliable methods of gas concentration measurement. In a typical NDIR method, the selective absorption of infrared radiation by certain gas species of interest is measured to determine the concentration of the target gas in a sample. This has a wide variety of applications—for example, NDIR measurements detecting absorption of radiation by carbon dioxide and other gases, such as carbon monoxide or hydrocarbons, are commonly used to monitor atmospheric composition or automotive exhaust, as well as in fire detectors.

A conventional NDIR instrument typically comprises the following elements:

a source of radiation (usually infrared), such as an incandescent lamp or another electrically heated element that serves as a blackbody emitter, e.g. a silicon carbide rod or nichrome filament;

a narrow bandwidth interference filter arranged to ensure that only radiation wavelengths absorbed by the gas of interest are measured;

a gas chamber for containing a sample including the target gas of interest; and a photodetector for detecting radiation transmitted by the sample and transforming the intensity of the detected radiation into an electrical signal.

Such a device is termed a "one channel" NDIR sensor and represents the simplest type of NDIR device. This type of instrument is relatively inexpensive, but does not provide any kind of compensation for instrument drift over time which may occur due to the radiation source and/or the photodetector ageing, or accumulation of dirt and dust in the optical path, for example. As a result, "one channel" NDIR instruments need to be calibrated relatively often. In addition, inaccuracies can arise due to changes in the ambient conditions, such as humidity and temperature, which may affect the performance of the radiation source and/or emitter.

The traditional way of compensating for such instabilities is to introduce a second optical channel. Such "two channel" NDIR sensors have a signal channel and a reference channel. The signal channel operates in exactly the same way as the "one channel" device described above, with the wavelength of the band pass filter adjusted to the absorption wavelength(s) of the gas of interest.

The reference channel usually works in another wavelength band, at which the target gas species does not absorb. This provides a base line for the signal channel. The differential signal between the signal and reference channels, normalized on reference channel intensity, gives an absorption signal which is stable with respect to any intensity drift resulting from the radiation source (or detector). In typical "two channel" sensors, the source of radiation has a wide spectral output, comprising both the signal and reference wavelengths. The use of a reference channel working on a wavelength where the target gas does not absorb has been found to provide a high degree of compensation of source radiation drift, and thus good measurement accuracy.

However, despite this improvement in stability, the provision of a second channel significantly increases the power consumption of the sensor as compared with one channel devices. The reference channel consumes a similar amount of power to that used by the signal channel, thus halving the power efficiency of the device. Two channel instruments also require additional components (including at least a second waveband filter and photodetector) and unavoidably give rise to a more complex and hence expensive chamber design. As a result, for low cost, low power NDIR instruments it is still desirable to have a single channel, in spite of the drift that may occur over time.

The power consumption of the device is also increased by the use of an incandescent bulb as the source of radiation, which is used in the vast majority of both one and two channel devices. Such radiation sources emit a very broad bandwidth of radiation (from visible to infrared), producing a significant amount of unusable energy, and hence are intrinsically inefficient. In addition, they are slow (typically, the response time is more than 100 milliseconds) and have significant power consumption (200 milliwatts or more). As such, these components are not suitable for portable, low power sensors which can typically support a power consumption of no more than 1-2 milliwatts.

Radiation sources such as light emitting diodes (LEDs), instead, are very fast (the response time is of the order of a few microseconds) and can be used in regimes having a power consumption of less than one milliwatt. LEDs are also far more power efficient than bulbs, converting a greater proportion of the input electrical power into radiation and emitting a relatively narrow bandwidth, corresponding closely to an absorption wavelength of the target gas. Likewise, semiconductor based photovoltaic (photodiode) detectors have a very fast response time. However, LED/photodiode pairs suffer from the considerable problem that the output signal depends significantly on temperature. This is as a result of variations in the wavelength and intensity of the emitted radiation as well as changes in the electrical response of the photodiode. These temperature dependencies have a fundamental nature and cannot be avoided in the design of the LED or photodiode. In practice, the level of temperature dependence is such that LEDs and photodiodes cannot be used in a one channel device since the signal output will be highly inaccurate.

Techniques have been proposed for utilizing LEDs and photodiodes in two channel designs but, apart from the increased power consumption and part count, these also encounter problems since the waveband emitted by an LED is inherently narrow and as such cannot typically provide both an absorption wavelength (for the signal channel) and a reference wavelength. It is therefore necessary to make use of particularly complex chamber designs to implement a two channel design utilizing LEDs and photodiodes. In addition, the accuracy is still not optimal since even a very small temperature difference between the signal and reference photodiodes, or a slight mismatch in their parameters, will cause a significant loss of accuracy.

In accordance with the present invention, an optical absorption gas analyser for determining the concentration of a target gas in a sample is provided, comprising:

a chamber for containing the sample in use;

an optopair, comprising a light emitting diode (LED) arranged to emit radiation into the chamber and a photovoltaic radiation detector arranged to detect radiation transmitted through the chamber from the LED and to output a corresponding detection signal $S_S$;

a temperature sensor arranged in thermal contact with the LED and the photovoltaic radiation detector, and to output a temperature signal T representing the temperature of the optopair;

a memory having stored therein data representative of the baseline detection signal $S_T$ output by the optopair in the absence of the target gas as a function of the temperature of the optopair across a range of temperatures; and a processor adapted to generate a differential detection signal $S_A$ indicative of the concentration of target gas in the sample by retrieving from the memory the baseline detection signal $S_T$ corresponding to the temperature signal T and calculating the difference between the detection signal $S_S$ and the baseline detection signal $S_T$.

The provision of a temperature sensor, stored baseline data and processor in this way effectively acts as a virtual reference channel, but without the disadvantages associated with the use of a traditional, optical reference channel. The baseline signal retrieved from the memory is the true baseline of the optopair forming the sole "signal" channel, and is therefore not reliant on any additional components, such as a reference photodetector. As such, problems associated with mismatched parameters or temperature variations are eliminated. There is also no need for a complex chamber design since a single optical path through the sample is sufficient. In addition, the accuracy of measurements from a typical temperature sensor is generally much better than that from any optopair.

The result is that the output signal $S_A$ accurately represents the signal variation caused by any target gas present in the chamber, and not by changes in temperature, which are removed by subtracting the baseline signal $S_T$. This makes it possible to implement a single channel device using an LED/photovoltaic (photodiode) optopair. The power requirements of the virtual reference channel are minimal. The resulting device therefore has an extremely low power consumption compared with conventional designs, whilst maintaining high measurement accuracy. The use of an LED/photovoltaic optopair also makes it possible to further reduce power consumption by a significant amount by pulse operating the optopair, which is not possible in conventional bulb based systems due to the very slow response times of the elements.

The differential signal $S_A$ can be used as the sensor output to provide a measure of the concentration of the target gas in the sample. However, in a preferred embodiment, the processor is further adapted to generate a normalised detection signal $S_N$, where: $S_N = S_A/S_T = (S_S - S_T)/S_T$. This provides a dimensionless output which is dependent on target gas concentration but not temperature.

The waveband of radiation emitted by the LED should include at least one absorption wavelength of the target gas. In order to minimise power wastage, the waveband emitted by the LED is preferably as narrow as possible: for instance, the bandwidth is preferably less than or equal to about 1 micron. However, the minimum width of the waveband is limited by expected variations in the wavelengths emitted by the LED caused by changes in temperature—the emitted waveband should be broad enough to accommodate such shifts whilst still covering the absorption wavelength of the target gas. In practice, the wavelengths (and waveband width) emitted by the LED will be selected based on the absorption spectra of the target gas. For instance, methane has a strong absorption peak at around 3.2 to 3.4 microns wavelength and it has been found that an LED emitting across the waveband 2.7 to 3.8 microns is well adapted for this application. However, different wavebands may be selected for different target gases.

The photovoltaic radiation detector is preferably adapted to detect radiation in a waveband at least overlapping that of the radiation emitter and including an absorption wavelength of the target gas. As such, the operating wavebands of the two elements need not be identical but should both include at least one (and the same) wavelength which is absorbed by the gas of interest. To tune the optopair to an appropriate waveband region, the analyser preferably further comprises a spectral filter disposed between the LED and the photovoltaic radiation detector for controlling the waveband of radiation detected, preferably an interference filter. In particularly preferred examples, the spectral filter is integral with the LED. Advantageously, the optopair emits and detects infrared radiation.

In preferred embodiments, the LED is a narrow band gap semiconductor based LED and the photovoltaic radiation detector is a narrow band gap semiconductor based detector, wherein the narrow band gap semiconductors preferably comprise InGaAs, PbS or PbSe. However, any other LED/photovoltaic elements having fast response times could be used.

As noted above, the temperature sensor is arranged to be in thermal contact with the LED and photovoltaic detector in order to measure the actual temperature of the optopair rather than the ambient temperature and thereby improve the accuracy of the virtual reference channel. Thermal contact can be achieved in a number of ways. Advantageously, the LED, photovoltaic radiation detector and temperature sensor are disposed adjacent to one another, preferably arranged on the same or adjacent faces of the chamber. Arranging the elements in close proximity to one another in this way helps to ensure that a common temperature will be maintained. In particularly preferred embodiments, the LED, photovoltaic radiation detector and temperature sensor are mounted on a thermally conductive plate. Alternatively, thermally conductive paint or foil could be used to connect the components.

Many forms of temperature sensor could be used such as a thermopile, or a platinum or semiconductor thermo resistor. However, in preferred embodiments, the temperature sensor comprises a semiconductor bandgap temperature sensor. For example, the sensor may comprise a p-n junction, a voltage across which will vary in proportion to the temperature. An integrated microchip may be provided for controlling the sensor and outputting the temperature signal. Temperature sensors of this sort provide a very high accuracy.

The baseline data can be stored in the memory in any convenient form, the choice of which may depend on the accuracy required of the device and the memory capacity available. In preferred examples, the data stored in the memory takes the form of a function (i.e. $S_T(T)$, usually a curve) or a table.

Baseline data is preferably made available for the full range of temperatures likely to be encountered by the device in situ. Therefore, preferably, the data stored in the memory comprises data representative of the baseline detection signal $S_T$ output by the optopair in the absence of the target gas as a function of the temperature of the optopair across a temperature range of at least 0° C. to +40° C., preferably approximately −30° C. to +60° C.

For high accuracy, the baseline data should include a large number of points: preferably no fewer than 15 across the temperature range and more preferably in excess of 100. In preferred implementations, the data stored in the memory includes values of $S_T$ for each temperature interval within the temperature range, where the temperature interval is less than or equal to 1° C., preferably less than or equal to 0.5° C. In particularly preferred examples, the baseline data is stored in the memory as at least one continuous function. Advantageously, the function may be approximated by a plurality of polynomial functions, each corresponding to a predetermined temperature range within the working temperature range of the sensor (e.g. −30° C. to +60° C.). For example, a polynomial function may be stored for each of four temperature ranges of approximately equal size. The accuracy of $S_T$ provided by the algorithm and processor is preferably of the order of $10^{-4}$.

The baseline data could be measured from the optopair prior to assembly of the device and later recorded in the memory. However, preferably, the processor is further adapted to, in a data capture mode, record the detection signal $S_S$ output by the optopair against the temperature signal T in the memory as the optopair is subjected to a change in temperature, to thereby provide the data representative of the baseline detection signal $S_T$. Thus the analyser itself is able to measure and record the baseline data during manufacture, which not only simplifies the process but improves the accuracy since the temperature is measured using the same sensor as will be used in the field. The temperature of the optopair can be varied, for example, by passing the optopair through an oven in the manufacturing process.

Since LEDs and photovoltaic detectors are highly stable over time, the baseline data recorded at manufacture should vary little during the sensor's lifetime. However, to provide confirmation that the baseline data corresponds accurately to the optopair, the processor is preferably further adapted to, in a self diagnostic mode, retrieve from the memory the baseline detection signal $S_T$ corresponding to the temperature signal T and compare the retrieved baseline detection signal $S_T$ with the detection signal $S_S$ from the optopair to determine whether the stored baseline accurately represents that of the optopair. This self-diagnostic routine should be carried out in the absence of any target gas, which may be achieved for example by immersing the analyser in a test gas of known content. Preferably, this check is performed each time the analyser is switched on.

The outcome of the comparison can be used in a number of ways. In one implementation, should the retrieved baseline signal $S_T$ be found not to match the measured $S_S$ signal, an indicator may be activated to alert the operator and/or request maintenance. However in preferred examples, the processor may be further adapted to determine a scaling factor F from the outcome of the comparison, and to apply the scaling factor to the baseline data $S_T$, generating a scaled temperature baseline, $S'_T$. The scaled baseline $S'_T$ is then used by the processor in the generation of the differential signal $S_A (=S_S-S'_T)$. Scaling the baseline signal in this way enables the analyser to take account of changes in the optical response of the optopair which may occur over time, for example caused by dust accumulating between the LED and the photodetector. The scaling factor F can be determined in a number of ways. For example, the magnitude of the sensing signal $S_S$ at the current temperature could be compared with that of the baseline signal $S_T$ at that temperature, and the ratio of the two values used as the scaling factor F.

As noted above, the use of a LED/photovoltaic optopair gives rise to the possibility of pulse-operating the optopair, for example by means of pulse width modulation. Hence, the analyser preferably further comprises a controller adapted to control the supply of power to the optopair, wherein the controller is adapted to intermittently power the LED with discrete pulses of power according to a low duty cycle of less than 50%. In preferred examples, the pulses have duration of between 15 and 100 microseconds, preferably approximately 20 microseconds. The duty cycle advantageously has a period of between 100 microseconds and 10 seconds. Preferably, the duty cycle is between 0.01% and 50%, preferably around 0.05%. Power savings of a factor exceeding 100 (compared with conventional bulb based NDIR systems) are possible.

Intermittent operation in this way also makes it possible to increase the sensitivity of the analyser since the discrete pulses can be arranged to have an intensity (power) greater than would be manageable in a continuous operation regime. This is because a short pulse of radiation has a better signal to noise ratio than a longer pulse of the same energy (and hence lower intensity): for constant energy, as the pulse width (duration) increases, the signal amplitude (intensity) decreases linearly, but the noise decreases as a square root function—i.e. less quickly than the intensity.

Another factor which can affect the detection signal output by the optopair is the relative humidity (RH) in which the analyser is operating. In particularly preferred embodiments, therefore, the analyser further comprises a humidity sensor adapted to detect the relative humidity of the sample in the chamber, and to output a corresponding humidity signal H. Various types of humidity sensor are known and could be utilised for this purpose. In preferred implementations, the humidity sensor comprises a semiconductive element, the surface conductivity of which varies with RH and is measured to provide a signal representative of humidity. The humidity signal can be used in a number of ways. In one example, the processor is further adapted to compare the humidity signal H with a predetermined humidity threshold and activate an indicator if the predetermined humidity threshold is exceeded. This alerts the user to the fact that the sensor is operating outside of its intended RH range and that the measurement accuracy may be compromised as a result.

However, in particularly preferred embodiments, the analyser is further adapted to compensate the output detection signal for variations in RH. Hence, preferably, the memory additionally has stored therein data representative of the baseline detection signal $S_{RH}$ output by the optopair in the absence of the target gas as a function of the relative humidity (RH) of the sample in the chamber across a range of RH; and the processor is further adapted to generate a second differential detection signal $S_B$ indicative of the concentration of target gas in the sample by retrieving from the memory the baseline detection signal $S_{RH}$ corresponding to the humidity signal H and calculating: $S_B=S_A-S_{RH}$. The variations in the signal $S_B$ are thus representative of target gas within the sample and not temperature or RH changes.

The analyser could be connected to an external power source in order to supply power to the radiation source and processing components. However, it is preferred that the analyser further comprises a power source so that the device is fully portable. Preferably the power source comprises a battery, solar cell or solar-powered battery. In particularly preferred embodiments, a highly efficient solar battery (up to 28% efficient) is provided, which can deliver several milliwatts of energy even in low illumination, significantly economizing on battery power. If these requirements are satisfied, the lifetime of the sensor could exceed one year without recharging or replacing the battery.

Preferably, the chamber is provided with at least one aperture for gas ingress from the surrounding atmosphere. This enables an atmosphere to be monitored in real time, for example by diffusion of the atmosphere under test or via an aspirator. However, in alternative situations, the sample could be input to the chamber by an operator for evaluation. For example, an atmosphere could be sampled by absorption into a carbon substrate, which is then heated to release the absorbed gas, which can be transferred into the detection chamber.

Also provided is a method of manufacturing an optical absorption gas analyser as described above, the method comprising:

subjecting the optopair to a change in temperature while monitoring the detection signal $S_S$ and the temperature signal T; and recording the detection signal $S_S$ output by the optopair against the temperature signal T in the memory, to thereby provide the data representative of the baseline detection signal $S_T$.

By measuring the baseline directly from the optopair and using temperature measurements from the onboard temperature sensor in this way, extremely high accuracy of the stored data is ensured. As noted above, the step of recording the baseline in this way is preferably performed by the onboard processor.

The change in temperature can be implemented in various ways, for instance by heating the sensor in one or more ovens during the manufacturing process. The baseline data could be established by taking measurements of the optopair output at a number of discrete temperature points. However, preferably, the temperature of the optopair is swept across a range at a rate of change, for example, of not more than 0.1° C./minute, and the value of the baseline detection signal is recorded continuously at intervals of no more than 1° C., preferably less than or equal to 0.5° C. In this way, a highly accurate baseline is established leading to very accurate measurements. Preferably, the temperature range is at least 0° C. to +40° C., preferably approximately −30° C. to +60° C.

An example of an optical absorption gas analyser and method of manufacture will now be described with reference to the accompanying drawings, in which.

Figure 1:
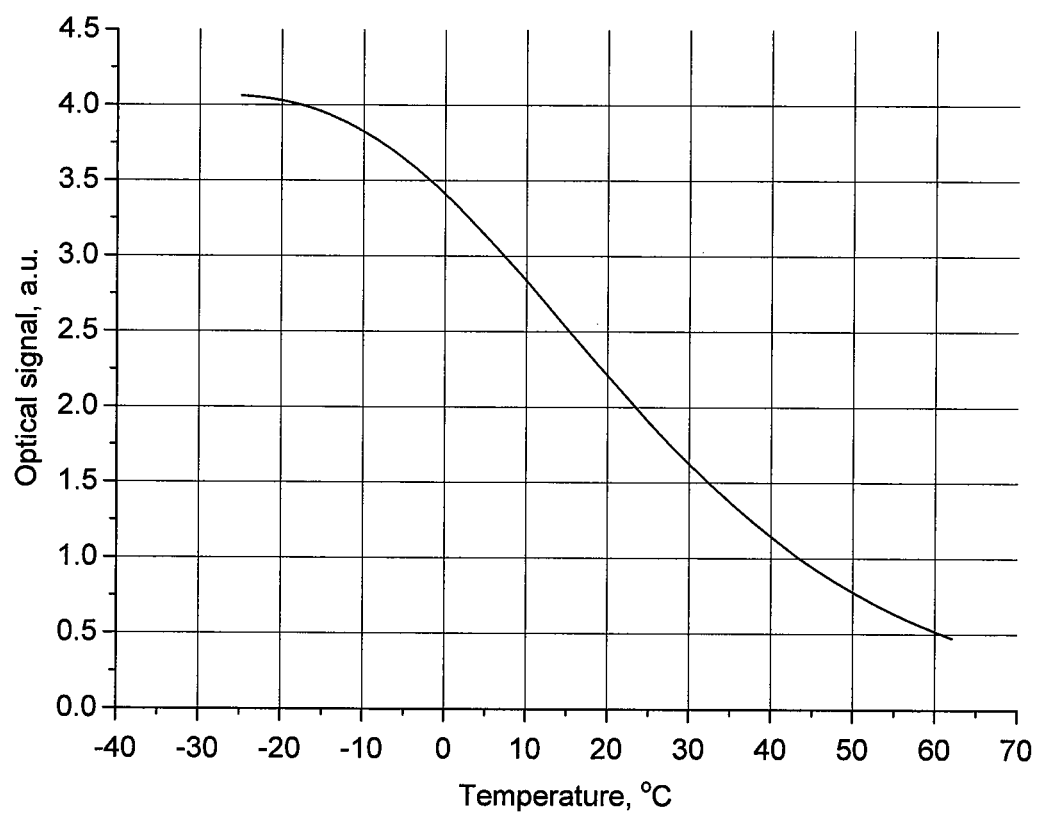
FIG. 1 is a graph showing a baseline signal for an exemplary LED/photovoltaic optopair, illustrating its significant variation with temperature.

In a LED/photovoltaic optopair, the output signal from the radiation detector has been found to vary by as much as a factor of 5 across a typical range of working temperatures. FIG. 1 illustrates this intrinsic temperature dependence in arbitrary units for an exemplary optopair operating at temperatures between around −30° C. and +60° C., in the absence of any absorption due to target gas. This intrinsic variation amounts to a baseline signal for the optopair in question.

In comparison, signal variations caused by the presence of target gas between the optopair elements are small: for example, increasing the concentration of methane from 0% vol. to 100% vol. will typically lead to a change in the optical output signal from the detector of no more than about 5%. As a result, gas concentration measurements taken from the optical signal alone will be vastly compromised by changes in the optopair's temperature.

Figure 2:
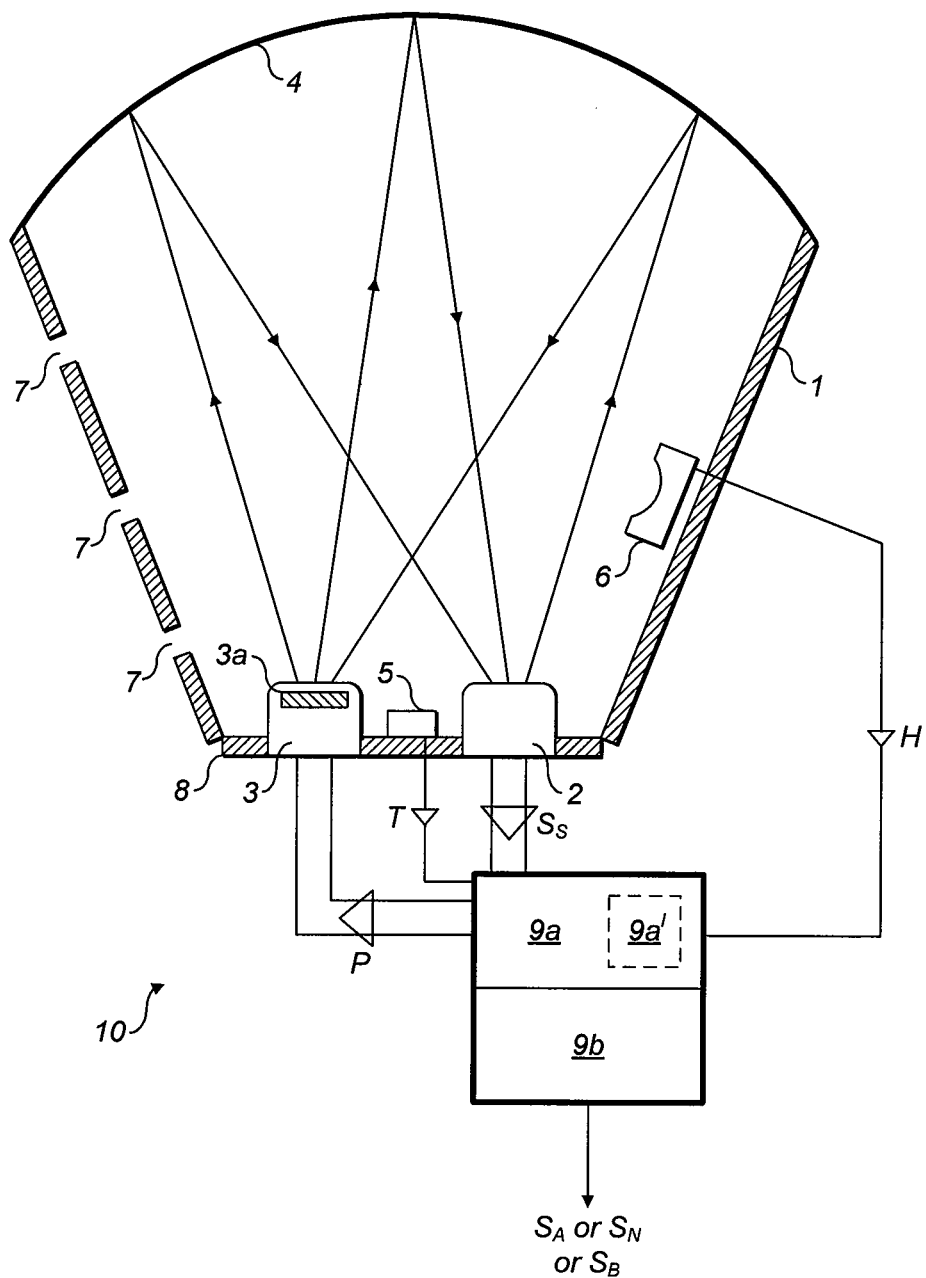
FIG. 2 shows an embodiment of an optical absorption gas analyser.

FIG. 2 shows an embodiment of a NDIR analyser which provides a virtual reference channel. The analyser 10 includes a sample chamber 1 which contains the gas sample to be tested. Apertures 7 are provided to place the chamber interior in fluid communication with an environment under test, although in other embodiments these could be omitted if the sample is to be introduced to the chamber manually.

An optopair comprising a LED radiation emitter 3 and a corresponding photovoltaic (photodiode) detector 2 is arranged to view the interior of the chamber 1. The LED 3 emits radiation at a predetermined wavelength or waveband which includes at least one wavelength known to be absorbed by the target gas of interest. For example, methane is known to absorb radiation at 3.2 to 3.4 microns wavelength. In this example, the radiation emitted by the LED is infrared, having a waveband of 2.75 to 3.8 microns. In order to control the wavelength of the radiation more precisely, a narrow spectral filter 3a may preferably be disposed between the LED 3 and the detector 2. In the present example, the filter 3a is an interference filter formed integrally with the LED 3. In this example, the filter 3a passes a waveband of 3.225 to 3.375 microns. The radiation is transmitted through the chamber 1, passing through the sample gas, and arrives at detector 2 which generates a corresponding electrical output signal dependent on the intensity of received radiation. The detector 2 is configured to detect radiation at wavelengths at least overlapping with that emitted by the LED (and passed by the filter) and including the absorption wavelength of the target gas.

The LED 3 and photovoltaic detector 2 are preferably based on narrow band gap semiconductors such as InGaAs, PbS or PbSe, which have a fast response time of the order of 5 to 10 microseconds.

In this example, the radiation is directed from the LED 3 to the detector 2 by a mirror 4, here a spherical mirror defining a surface of the chamber 1. However, this is not essential since the optopair elements could be arranged at opposing ends of the chamber 1. Alternatively, any other types of optical guiding elements such as prisms could be used to direct the radiation between the LED 3 and the detector 2 as desired. This example has the advantage that the optopair components can be disposed adjacent one another, which is beneficial for reasons described below.

The detector 2 outputs a sensing signal $S_S$ to a processor 9a as will be described further below. In this example, the processor 9a is combined with a controller 9b which controls the power supply P to the LED 3. The LED 3 could be powered continuously during operation but it is preferred that the controller implements a low duty cycle pulsed power regime wherein a series of discrete pulses power the LED 3, in order to reduce power consumption. This also makes it possible to increase the intensity of each individual pulse, thereby enhancing the sensitivity of the instrument. The controller 9b also controls the amplitude of the pulses.

In preferred implementations, the pulses have a duration of between 15 and 100 microseconds, preferably between 15 and 30 microseconds, most preferably around 20 microseconds, and a duty cycle of around 0.04% on any convenient frequency. However, the duty cycle could be anywhere between 0.01% and 50%, preferably around 0.05%. In particular examples, the power signal P has a period of between 100 microseconds and 10 seconds.

Also provided in the analyser 10 is a temperature sensor 5 arranged in thermal contact with both elements of the optopair so as to measure the temperature thereof. The temperature sensor 5 outputs a signal T representative of the measured temperature. In this example, the sensor 5 is a band gap temperature sensor, comprising a semiconductor structure incorporating a p-n junction and a microcontroller arranged to measure the voltage across the junction. This voltage varies in proportion to the temperature and so provides an accurate temperature measurement. The temperature signal T is also provided to the processor 9a.

The processor 9a includes a memory 9a' (although in other examples this could be provided separately). In the memory 9'a is stored data representing the temperature baseline $S_T$ of the optopair 2/3. This could be stored in the form of a function, a table or a curve akin to that depicted in FIG. 1. The temperature baseline $S_T$ is the signal $S_S$ output by the detector 2 in the absence of any target gas across a range of temperature values. Where the data takes the form of a table, for accuracy, the data should be stored at high resolution; that is, numerous $S_T$ values should be stored from across the temperature range—no fewer than 15 and, ideally, more than 100. $S_T$ values are preferably stored for every temperature value in the range at intervals of no more than 1° C., although this need not be constant across the whole temperature range. The data preferably covers the full range of working temperatures to which the analyser may be subjected in use. As such, the data preferably covers at least the range 0° C. to +40° C. and more preferably extends from −30° C. to +60° C.

In particularly preferred examples, the baseline data is stored in the form of a continuous function or a set of functions, each one corresponding to a portion of the full temperature range. For example, a continuous function may be closely approximated by a number of polynomial functions, each valid across a certain range of temperatures. In one instance, the full working temperature range may be divided into four portions of approximately equal size and a function stored for each, e.g.:

$$(-30°\ C. \leq T < -10°\ C.) S_T = f_1(T)$$

$$(-10°\ C. \leq T < +20°\ C.) S_T = f_2(T)$$

$$(+20°\ C. \leq T < +40°\ C.) S_T = f_3(T)$$

$$(+40°\ C. \leq T < +60°\ C.) S_T = f_4(T)$$

where $f_1$, $f_2$, $f_3$ and $f_4$ each represent functions of T which may be derived, for example, by curve-fitting each section of the baseline data obtained from the optopair. Typically, the functions are polynomial functions of the third order. The specific functions will of course vary between optopairs, as will the appropriate extend and number of the temperature ranges.

In use, to determine the concentration of target gas in the sample, the processor 9a retrieves the baseline value $S_T$ for the presently detected temperature T, according to the signal from temperature sensor 5, from the memory 9a'. The processor generates a differential signal $S_A$ from the detection signal $S_S$ supplied by the detector 2:

$$S_A = S_S - S_T$$

Since the detection signal $S_S$ is dependent on the concentration of target gas in the chamber and the temperature, whereas the baseline $S_T$ depends on temperature only, the resulting differential signal $S_A$ represents the contribution made by the target gas only. This therefore provides an accurate measure of the target gas present.

If desired, the processor 9a could generate a normalised signal $S_N$, which gives a dimensionless output dependent on the concentration of target gas only (and not the temperature):

$$S_N = S_A / S_T = (S_S - S_T) / S_T$$

Figure 3:
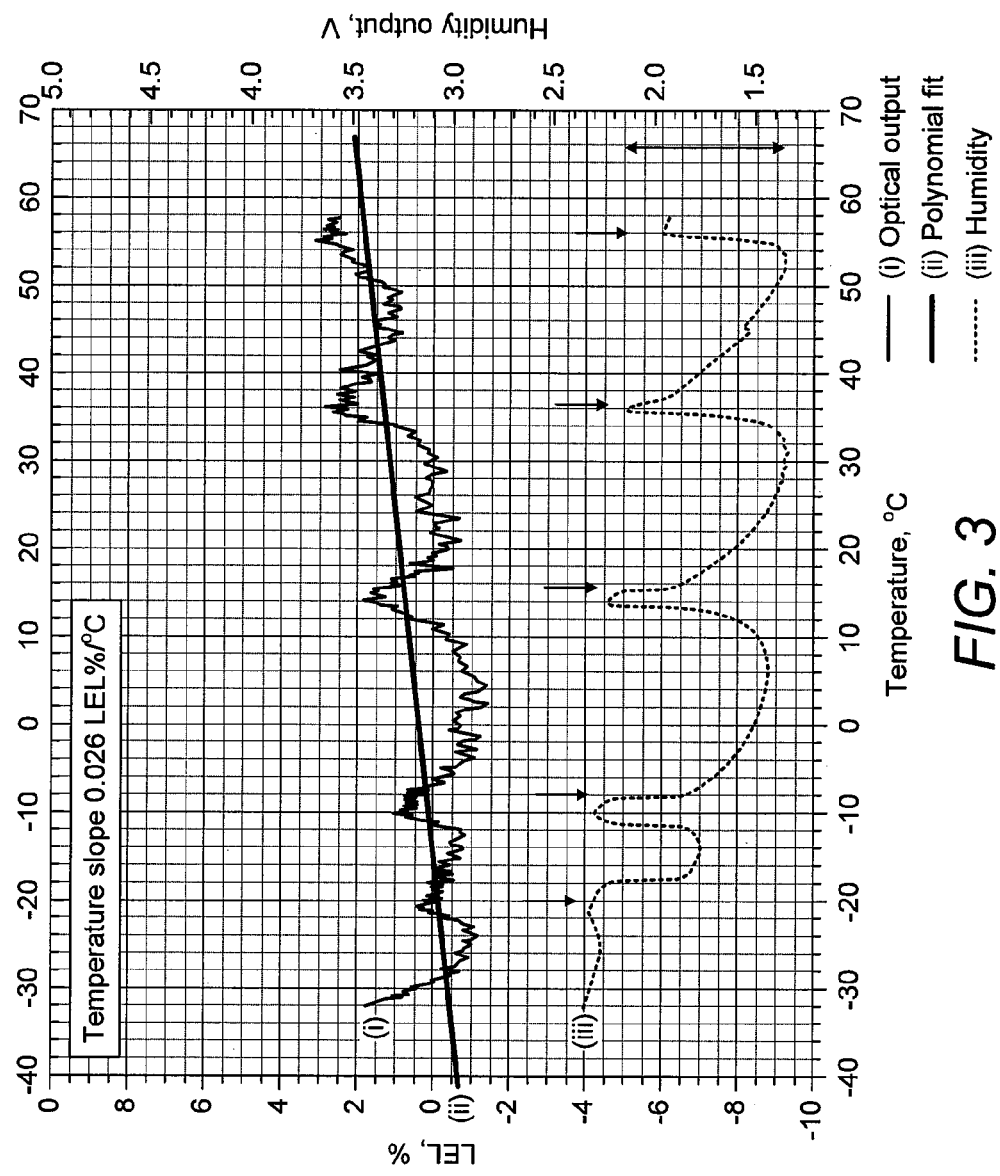
FIG. 3 is a graph showing the differential output signal of the optical absorption gas analyser of FIG. 2 across a range of temperatures and varying relative humidity in the absence of any target gas.

FIG. 3 shows results achieved using this approach in an exemplary sensor. Trace (i) shows the differential signal $S_A$ output by the processor in the absence of any target gas across a range of temperatures from −30° C. to +60° C., converted into units representing percentage units of the lower explosion limit (LEL) of methane. It can be seen that the temperature drift of signal $S_A$ does not exceed 2% LEL across the full temperature range. Trace (ii) is a best line fit of data (i) and has a gradient of around 0.026% LEL/C. Thus, on average, for every 1° C. increase in temperature the signal increases by only a fraction of a percent. This is a vast improvement on the intrinsic 500+% change in the raw optopair signal, and is well within required performance limits. Experiments carried out by the inventor show that after initial thermal cycling (in the range of about 0° C. to 65° C. over 24 hours), the optopair exhibits very good thermal stability and repeatability, sufficient to measure, for instance, methane concentration to an accuracy of 1% LEL.

The peaks in the signal $S_A$ (trace (i)) are a result of the experimental technique, in which the temperature of the optopair was raised in a series of steps, the values of which are indicated by the arrows "Temp Set".

The changing temperature also affects the relative humidity (RH) of the sample, which in turn has an impact on the sensor signal $S_S$. Variations in RH can also result from the local environment in which the sensor is deployed. Therefore, in preferred embodiments, a humidity sensor 6 is provided in the chamber 1. Many different types of humidity sensor could be employed but, in this case, a semiconductor humidity sensor is used, the surface of which is exposed to the sample within the chamber 1. The electrical conductivity of the sensor's surface changes according to the RH of the sample and this is measured to generate a humidity signal, H. The humidity signal H can also be supplied to the processor 9a.

As FIG. 3 illustrates, temperature variation across the working range can, by itself, cause RH variation of as much as 30%. The above described virtual reference channel can compensate well for this as shown by trace (i). However, if the ambient RH changes independently of temperature (e.g. as a result of deploying the sensor in a high RH environment), it is desirable to provide a second virtual reference channel to deal with this. Preferably, therefore, the memory 9a' also stores RH baseline data $S_{RH}$ across a range of RH values expected to be encountered in the field. As for the temperature baseline, the RH baseline can be stored in the form of a table, function or curve. The processor 9a generates a second differential signal $S_B$, by retrieving the relevant value of $S_{RH}$ based on the currently received humidity signal H, and calculating:

$$S_B = S_A - S_{RH}$$

In an alternative embodiment, rather than store a RH baseline, the value of H is compared with a predetermined threshold or range and, should it be found that H exceeds the threshold or falls outside the range, an indicator can be activated to alert the operator to the fact that the sensor is not within its operational RH range, and that as a result the measured gas concentration may not be accurate.

As mentioned above, it is preferable for the LED 3 and detector 2 to be disposed adjacent one another, e.g. on the same surface of the chamber 1, and this is to ensure that both components are at substantially the same temperature. For the same reason, the temperature detector 5 is preferably placed alongside or between the optopair components. To improve thermal contact, the three components are preferably mounted on a common thermally conductive plate 8 as shown in FIG. 2. However in alternative implementations this could be achieved using conductive paint or foil, such as silver paint, for example.

The accuracy of the output signal $S_A$ (or $S_N$ or $S_B$) clearly depends on the accuracy of the recorded baseline data $S_T$ and the manner in which this is obtained is therefore important. Firstly, the baseline should be measured from the same optopair as fitted in the analyser, rather than from some test or sample component. This is because the parameters vary between apparently identical components to such an extent that the baseline measured from one optopair may not correspond sufficiently to that of another. The manufacturing of the analyser therefore includes a step of varying the temperature of the optopair (in the absence of any target gas) and recording its response. This can be achieved by passing the optopair through an oven. During this process, the temperature is preferably measured using the temperature sensor 5 provided in the analyser itself.

During this data recordal step, the temperature of the optopair is preferably swept continuously (by an oven or other apparatus) through the desired temperature range so as to maximise the number of data points available.

To streamline the manufacturing process, the onboard processor 9a is preferably configured to perform this data collection step during manufacture. Thus the processor 9a preferably stores instructions for storing the signal $S_S$ from the detector against the measured temperature T, which can be accessed by placing the device in a set-up mode. For example, the routine may involve monitoring the temperature T and upon the temperature T changing by a pre-defined increment $\Delta T$, sampling and recording the signal $S_S$.

In addition, the processor 9a may optionally include a routine for checking the accuracy of the stored baseline data against the actual performance of the optopair. This routine may be run automatically upon start up of the instrument or on-demand, but should be performed with the analyser exposed to a controlled atmosphere of zero target gas. This can be achieved by placing a test enclosure over the sensor, and filling the chamber 1 with a gas of known content. In this example, the check is carried out by comparing the value of the sensor signal $S_S$ with the expected temperature baseline value $S_T$ at the present temperature (known from the temperature signal T). If there is found to be a mismatch, which may be caused for example by the accumulation of dust in the optopair, the processor could output a signal activating an indicator to alert the operator to the problem. Alternatively, the processor could be programmed to take account of the mismatch by determining a scaling factor F to apply to the temperature baseline $S_T$. The scaling factor F could be provided in a number of ways. For example, the memory could be used to store a look-up table correlating mismatch amounts with appropriate F values. Alternatively, the processor could calculate the ratio $S_S/S_T$, which may provide an appropriate scaling factor F.

The scaling factor F is applied to the temperature baseline (and, if desired the humidity baseline $S_{RH}$) to generate a scaled baseline $S'_T = F \cdot S_T$. In determining the differential output $S_A$ (or $S_B$), the scaled baseline is used:

$$S_A = S_S - S'_T$$

$$S_B = S_S - S'_T - S_{RH}$$

The invention claimed is:

1. An optical absorption gas analyser for determining the concentration of a target gas in a sample, comprising:
   a chamber for containing the sample in use;
   an optopair, comprising a light emitting diode (LED) arranged to emit radiation into the chamber and a photovoltaic radiation detector arranged to detect radiation transmitted through the chamber from the LED and to output a corresponding detection signal $S_S$;
   a temperature sensor arranged in thermal contact with the LED and the photovoltaic radiation detector, and to output a temperature signal T representing the temperature of the optopair;
   a memory having stored therein data representative of the baseline detection signal $S_T$ output by the optopair in the absence of the target gas as a function of the temperature of the optopair across a range of temperatures, the memory further storing processor-executable instructions for causing the processor to:
      record the detection signal $S_S$ output by the optopair against the temperature signal T in the memory as the optopair is subjected to a change in temperature, to thereby provide and store the data representative of the baseline detection signal $S_T$ in the memory;
      generate a differential detection signal $S_A$ indicative of the concentration of target gas in the sample by retrieving from the memory the baseline detection signal $S_T$ corresponding to the temperature signal T; and
      calculate the difference between the detection signal $S_S$ and the baseline detection signal $S_T$; and
   a processor for executing the processor-executable instructions to:
      record the detection signal $S_S$ output by the optopair against the temperature signal T in the memory as the optopair is subjected to a change in temperature, to thereby provide and store the data representative of the baseline detection signal $S_T$ in the memory;
      generate a differential detection signal $S_A$ indicative of the concentration of target gas in the sample by retrieving from the memory the baseline detection signal $S_T$ corresponding to the temperature signal T; and
      calculate the difference between the detection signal $S_S$ and the baseline detection signal $S_T$.

2. An optical absorption gas analyser according to claim 1, wherein:
   the memory further stores processor-executable instructions for causing the processor to generate a normalised detection signal $S_N$, where:

$$S_N = S_A/S_T = (S_S - S_T)/S_T; \text{ and}$$

the processor is further for executing the processor-executable instructions to generate the normalised detection signal $S_N$.

3. An optical absorption gas analyser according to claim 1, wherein the waveband of radiation emitted by the LED includes an absorption wavelength of the target gas.

4. An optical absorption gas analyser according to claim 1 wherein the photovoltaic radiation detector is adapted to detect radiation in a waveband at least overlapping that of the LED and including an absorption wavelength of the target gas.

5. An optical absorption gas analyser according to claim 1, further comprising a spectral filter disposed between the LED and the photovoltaic radiation detector for controlling the waveband of radiation detected, preferably an interference filter.

6. An optical absorption gas analyser according to claim 5 wherein the spectral filter is integral with the LED.

7. An optical absorption gas analyser according to claim 1 wherein the optopair emits and detects infrared radiation.

8. An optical absorption gas analyser according to claim 1, wherein the LED is a narrow band gap semiconductor based LED and the photovoltaic radiation detector is a narrow band gap semiconductor based detector, wherein the narrow band gap semiconductors preferably comprise InGaAs, PbS or PbSe.

9. An optical absorption gas analyser according to claim 1, wherein the LED, photovoltaic radiation detector and temperature sensor are disposed adjacent to one another, preferably arranged on the same or adjacent faces of the chamber.

10. An optical absorption gas analyser according to claim 1, wherein the LED, photovoltaic radiation detector and temperature sensor are mounted on a thermally conductive plate.

11. An optical absorption gas analyser according to claim 1, wherein the temperature sensor comprises a semiconductor bandgap temperature sensor.

12. An optical absorption gas analyser according to claim 1 wherein the data stored in the memory takes the form of a function or table.

13. An optical absorption gas analyser according to claim 1, wherein the data stored in the memory comprises data representative of the baseline detection signal $S_T$ output by the optopair in the absence of the target gas as a function of the temperature of the optopair across a temperature range of at least 0° C. to +40° C., preferably approximately −30° C. to +60° C.

14. An optical absorption gas analyser according to claim 1, wherein the data stored in the memory includes values of $S_T$ for each temperature interval within the temperature range, where the temperature interval is less than or equal to 1° C., preferably less than or equal to 0.5° C.

15. An optical absorption gas analyser according to claim 1, wherein:
the memory further stores processor-executable instructions for causing the processor to retrieve from the memory the baseline detection signal $S_T$ corresponding to the temperature signal T and compare the retrieved baseline detection signal $S_T$ with the detection signal $S_S$ from the optopair to determine whether the stored baseline detection signal $S_T$ accurately represents that of the optopair; and
the processor is further for executing the processor-executable instructions to retrieve from the memory the baseline detection signal $S_T$ corresponding to the temperature signal T and compare the retrieved baseline detection signal $S_T$ with the detection signal $S_S$ from the optopair to determine whether the stored baseline detection signal $S_T$ accurately represents that of the optopair.

16. An optical absorption gas analyser according to claim 15, wherein:
the memory further stores processor-executable instructions for causing the processor to determine a scaling factor F from the outcome of the comparison, and to apply the scaling factor to the baseline detection signal $S_T$, generating a scaled temperature baseline, $S'_T$; and
the processor is further for executing the processor-executable instructions to determine the scaling factor F from the outcome of the comparison, and to apply the scaling factor to the baseline detection signal $S_T$, generating the scaled temperature baseline, $S'_T$.

17. An optical absorption gas analyser according to claim 1, further comprising a controller adapted to control the supply of power to the optopair, wherein the controller is adapted to intermittently power the LED with discrete pulses of power according to a low duty cycle of less than 50%.

18. An optical absorption gas analyser according to claim 17 wherein the pulses have a duration of between 15 and 100 microseconds, preferably approximately 20 microseconds.

19. An optical absorption gas analyser according to claim 17, wherein the duty cycle has a period of between 100 microseconds and 10 seconds.

20. An optical absorption gas analyser according to claim 17, wherein the duty cycle is between 0.01% and 50%, preferably around 0.05%.

21. An optical absorption gas analyser according to claim 1, wherein the analyser is a single optical channel analyser.

22. An optical absorption gas analyser according to claim 1, further comprising a humidity sensor adapted to detect the relative humidity of the sample in the chamber, and to output a corresponding humidity signal H.

23. An optical absorption gas analyser according to claim 22 wherein:
the memory further stores processor-executable instructions for causing the processor to compare the humidity signal H with a predetermined humidity threshold and activate an indicator if the predetermined humidity threshold is exceeded; and
the processor is further for executing the processor-executable instructions to compare the humidity signal H with the predetermined humidity threshold and activate the indicator if the predetermined humidity threshold is exceeded.

24. An optical absorption gas analyser according to claim 22, wherein:
the memory additionally has stored therein data representative of the baseline detection signal $S_{RH}$ output by the optopair in the absence of the target gas as a function of the relative humidity (RH) of the sample in the chamber across a range of RH;
the memory further stores processor-executable instructions for causing the processor to generate a second differential detection signal $S_B$ indicative of the concentration of target gas in the sample by retrieving from the memory the baseline detection signal $S_{RH}$ corresponding to the humidity signal H and calculating:

$$S_B = S_A - S_{RH}; \text{ and}$$

the processor is further for executing the processor executable instructions to generate the second differential detection signal $S_B$ indicative of the concentration of target gas in the sample by retrieving from the memory the baseline detection signal $S_{RH}$ corresponding to the humidity signal H and calculating:

$$S_B = S_A - S_{RH}.$$

25. A method of manufacturing an optical absorption gas analyser according to claim 1, the method comprising:
subjecting the optopair to a change in temperature while monitoring the detection signal $S_S$ and the temperature signal T; and
recording the detection signal $S_S$ output by the optopair against the temperature signal T in the memory, to thereby provide the data representative of the baseline detection signal $S_T$.

26. A method according to claim 25, wherein the temperature of the optopair is swept across a range and the value of the baseline detection signal is recorded continuously at intervals of no more than 1° C., preferably less than or equal to 0.5° C.

27. A method according to claim 26, wherein the temperature range is at least 0° C. to +40° C., preferably approximately −30° C. to +60° C.

* * * * *